(12) United States Patent
Masuda et al.

(10) Patent No.: US 7,146,207 B2
(45) Date of Patent: Dec. 5, 2006

(54) HEALTH ADMINISTRATION APPARATUS

(75) Inventors: Yasutoshi Masuda, Akashi (JP);
Shuichi Okabe, Akashi (JP); Shozo Kawanishi, Akashi (JP)

(73) Assignee: Yamato Scale Co., Ltd., Akashi (JP)

( * ) Notice: Subject to any disclaimer, the term of this patent is extended or adjusted under 35 U.S.C. 154(b) by 524 days.

(21) Appl. No.: 10/258,701

(22) PCT Filed: Oct. 19, 2001

(86) PCT No.: PCT/JP01/09191

§ 371 (c)(1),
(2), (4) Date: Oct. 24, 2002

(87) PCT Pub. No.: WO02/34132

PCT Pub. Date: Feb. 5, 2002

(65) Prior Publication Data
US 2003/0097081 A1 May 22, 2003

(30) Foreign Application Priority Data
Oct. 24, 2000 (JP) .............................. 2000-324136

(51) Int. Cl.
*A61B 5/05* (2006.01)
(52) U.S. Cl. ................... 600/547; 600/485; 600/409
(58) Field of Classification Search ................ 600/547, 600/485, 409; 348/65; 351/208
See application file for complete search history.

(56) References Cited

U.S. PATENT DOCUMENTS 5,579,782 A * 12/1996 Masuo ..................... 600/547
6,487,445 B1 * 11/2002 Serita et al. ................ 600/547
6,488,202 B1 * 12/2002 Seitz et al. ................ 235/78 R
6,516,221 B1 * 2/2003 Hirouchi et al. ............ 600/547

FOREIGN PATENT DOCUMENTS

| JP | 62-243535 | 10/1987 |
|---|---|---|
| JP | 6-217962 | 8/1994 |
| JP | 11-128199 | 5/1999 |
| JP | 2000-139869 | 5/2000 |
| JP | 2000-171288 | 6/2000 |
| JP | 2000-175875 | 6/2000 |
| JP | 2000-225100 | 8/2000 |
| JP | 2000-350710 | 12/2000 |

* cited by examiner

*Primary Examiner*—Max F. Hindenburg
*Assistant Examiner*—Fangemonique Smith
(74) *Attorney, Agent, or Firm*—Alleman Hall McCoy Russell & Tuttle LLP

(57) ABSTRACT

A health administration apparatus 10 is provided, which is capable of dispensing with a troublesome measuring operation such as to wrap a tape measure or the like around a part of concern of a human body by automatically finding the abdominal circumference (waist size) or the lumbar circumference (hip size) of a human body. The health administration apparatus 10 is configured to allow entry of body data of an examinee, including the height and weight of the examinee, and to be capable of finding the abdominal circumference of the examinee which is the circumferential size of a trunk part of the examinee by a computation based on the body data including the height and the weight of the examinee.

37 Claims, 3 Drawing Sheets

HEALTH ADMINISTRATION APPARATUS

TECHNICAL FIELD

The present invention relates to a health administration apparatus which is capable of automatically measuring the physical size of a characteristic part of the body of an examinee that is useful in judging the condition of health of the examinee.

BACKGROUND ART

Examples of conventional apparatuses capable of evaluating and monitoring the degree of obesity of a human body include a body fat meter, with which the user can measure the percent of his or her body fat to recognize the degree of his or her obesity and with which the user is capable of monitoring the degree of his or her obesity for health administration by periodically measuring the percent of his or her body fat.

The abdominal circumference, or the so-called waist size, which is the circumferential size of a trunk part, is the physical size of a part of a human body which is likely to have relation to the degree of obesity and which can be used as an indicator of the condition of health.

That is, by measuring the waist size of a human body, it is possible to obtain a measure in connection with the degree of obesity of the human body; if the user finds an increase in his or her waist size, the user can control his or her health condition by taking care of dietary habits and the like to prevent obesity.

Heretofore, however, it has been required that the waist size measurement be performed with use of a tape measure or the like and, hence, the measurement has been time-consuming. Specifically, it has been required that such a tape measure be wrapped around the waist part of a human body to achieve measurement and, hence, the measurement has been time-consuming. Particularly when the waist size measurement is to be performed for a group medical examination in a school or a workplace for example, much time is required because a large number of examinees should be subjected to the measurement.

The lumbar circumference, or the so-called hip size, which is the circumferential size of a hip part, is the physical size of another part of a human body which is likely to have relation to the degree of obesity. The hip size measurement, also, needs to be performed with use of a tape measure or the like and hence is time-consuming.

It is, therefore, desirable that the waist size or hip size be automatically found by computation, not by direct measurement with a tape measure or the like. It is also desirable that health-related information about a body be obtained on the basis of such a waist size or hip size.

Accordingly, it is an object of the present invention to provide a health administration apparatus which is capable of automatically finding the waist size or the hip size of a human body that can be used in evaluating the degree of obesity of the human body and which is capable of dispensing with direct measurement of the human body with a tape measure or the like.

DISCLOSURE OF INVENTION

In order to resolve the foregoing problems, a health administration apparatus according to the present invention is configured such that: the apparatus allows entry of body data of an examinee including the height and weight of the examinee; and the apparatus is capable of finding the abdominal circumference of the examinee which is the circumferential size of a trunk part of the examinee by a computation based on the body data including the height and the weight of the examinee.

With this health administration apparatus according to the present invention, it is possible to automatically find the abdominal circumference (waist size) of an examinee which is the circumferential size of a trunk part of the examinee as well as to dispense with a troublesome measuring operation such as to wrap a tape measure or the like around the trunk of a human body to find the abdominal circumference in judging the degree of obesity of the human body.

A health administration apparatus according to the invention may be configured such that: the apparatus allows entry of body data of an examinee including the height and weight of the examinee;

the apparatus has impedance measurement means capable of measuring the impedance of the body of the examinee via electrodes brought into contact with extremities of the body of the examinee; and the apparatus is capable of finding the abdominal circumference of the examinee which is the circumferential size of a trunk part of the examinee by a computation based on the body data including the height and weight of the examinee and the impedance of the body of the examinee.

This health administration apparatus according to the invention is capable of automatically finding the abdominal circumference of an examinee.

A health administration apparatus according to the invention may be configured such that: the apparatus allows entry of body data of an examinee including the height and weight of the examinee;

the apparatus has body fat percent measurement means capable of finding the body fat percent of the examinee based on the impedance of the body of the examinee that is measured via electrodes brought into contact with extremities of the body of the examinee; and the apparatus is capable of finding the abdominal circumference of the examinee which is the circumferential size of a trunk part of the examinee by a computation based on the body data including the height and weight of the examinee and information about the body fat of the examinee measured by the body fat percent measurement means.

With this health administration apparatus according to the invention, it is possible to automatically find the abdominal circumference of an examinee as well as to obtain information about the body fat of the examinee by the body fat percent measurement means.

A health administration apparatus according to the invention may be configured such that: the apparatus allows entry of body data of an examinee including the height and weight of the examinee;

the apparatus has body fat percent measurement means capable of finding the body fat percent of the examinee based on the impedance of the body of the examinee that is measured via electrodes brought into contact with extremities of the body of the examinee; and the apparatus is capable of finding the abdominal circumference of the examinee which is the circumferential size of a trunk part of the examinee by a computation based on the body data including the height, weight, and body fat percent of the examinee.

With this health administration apparatus according to the present invention, it is possible to automatically find the abdominal circumference of an examinee as well as to measure the body fat percent of the examinee that is usable as one of indicators of the condition of health by the body fat percent measurement means.

A health administration apparatus according to the invention may be configured such that: the apparatus allows entry of body data of an examinee including the height, weight, and age of the examinee;

the apparatus is capable of finding the abdominal circumference of the examinee which is the circumferential size of a trunk part of the examinee by a computation on the body data based on a predetermined computing formula;

the computing formula is created by statistical processing of correlations between the abdominal circumferences of a large number of human bodies serving as samples that are measured by a physical measurement and body data of the human bodies as the samples; and the computation based on the computing formula for finding the abdominal circumference of the examinee is performed using the weight, age, and BMI of the examinee.

With this health administration apparatus according to the present invention, it is possible to find the abdominal circumference of an examinee from the body data of the examinee including the height, weight, and age of the examinee based on the computing formula created by statistical processing of correlations between the abdominal circumferences of the large number of human bodies serving as samples and body data of the human bodies including the heights, weights, and ages of the human bodies.

Thus, it is possible to automatically find the abdominal circumference (waist size) of an examinee which is the size of the circumference of a trunk part of the examinee as well as to dispense with a troublesome measuring operation such as to wrap a tape measure or the like around the trunk of a human body to find the abdominal circumference in judging the degree of obesity of the human body.

A health administration apparatus according to the invention may be configured such that: the apparatus allows entry of body data of an examinee including the height, weight, and age of the examinee;

the apparatus has body fat percent measurement means capable of finding the body fat percent of the examinee based on the impedance of the body of the examinee that is measured via electrodes brought into contact with extremities of the body of the examinee;

the apparatus is capable of finding the abdominal circumference of the examinee which is the circumferential size of a trunk part of the examinee by a computation on the body data including the height, weight, and body fat percent of the examinee based on a predetermined computing formula;

the computing formula is created by statistical processing of correlations between the abdominal circumferences of a large number of human bodies serving as samples that are measured by a physical measurement and body data of the human bodies as the samples; and the computation based on the computing formula for finding the abdominal circumference of the examinee is performed using the weight, age, body fat percent, and BMI of the examinee.

With this health administration apparatus according to the present invention, it is possible to find the abdominal circumference of an examinee from the body data of the examinee including the height, weight, and age of the examinee based on the computing formula created by statistical processing of correlations between the abdominal circumferences of the large number of human bodies serving as samples and body data of the human bodies including the heights, weights, and ages of the human bodies, as well as to measure the body fat percent of the examinee that is usable as one indicator of the condition of health by the body fat percent measurement means.

The computing formula for finding the abdominal circumference may be created on a sex basis by dividing the large number of samples to be used in creating the computing formula into a male group and a female group. Thus, the abdominal circumference of an examinee found from the body data including the height, weight, and the like of the examinee based on the computing formula can reflect differences essential to the difference in sex.

The health administration apparatus which is capable of finding the abdominal circumference may be configured to find quantitative information about visceral fat by a computation based on the abdominal circumference found.

Since the abdominal circumference of an examinee, which is the circumferential size of a trunk part of the examinee, is related to the amount of visceral fat adhering to the internal organs of the examinee, it is possible to find quantitative information about the visceral fat from the abdominal circumference. Visceral fat strongly influences the condition of health such as adult diseases and, hence, such quantitative information about visceral fat can be used as an important indicator in predicting the condition of health.

The health administration apparatus according to the present invention may be configured to be capable of finding the visceral fat cross-sectional area of the examinee by a computation on the abdominal circumference found with another predetermined computing formula, wherein said another computing formula is created by statistical processing of correlations between the actual visceral fat cross-sectional areas of the large number of human bodies as the samples that are measured by tomography and the abdominal circumferences of the human bodies as the samples.

With this health administration apparatus according to the present invention, it is possible to find the visceral fat cross-sectional area of an examinee from the examinee's abdominal circumference found based on the aforesaid another computing formula created by statistical processing of correlations between the visceral fat cross-sectional areas of the large number of human bodies as the samples and the abdominal circumferences of the human bodies.

On the other hand, a health administration apparatus according to the present invention may be configured such that: the apparatus allows entry of body data of an examinee including the height and weight of the examinee; and the apparatus is capable of finding the lumbar circumference of the examinee which is the circumferential size of a hip part of the examinee by a computation based on the body data including the height and weight of the examinee.

With this health administration apparatus according to the present invention, it is possible to automatically find the lumbar circumference (hip size) of an examinee, which is the circumferential size of a hip part of the examinee, as well as to dispense with a troublesome measuring operation such as to wrap a tape measure or the like around the hip of a human body to find the lumbar circumference in judging the degree of obesity of the human body.

A health administration apparatus according to the invention may be configured such that: the apparatus allows entry of body data of an examinee including the height and weight of the examinee;

the apparatus has impedance measurement means capable of measuring the impedance of the body of the examinee via electrodes brought into contact with extremities of the body of the examinee; and the apparatus is capable of finding the lumbar circumference of the examinee, which is the circumferential size of a hip part of the examinee, by a computation based on the body data including the height, weight, and impedance of the examinee.

This health administration apparatus according to the invention is capable of automatically finding the lumbar circumference of an examinee.

A health administration apparatus according to the invention may be configured such that: the apparatus allows entry of body data of an examinee including the height and weight of the examinee;

the apparatus has body fat percent measurement means capable of finding the body fat percent of the examinee based on the impedance of the body of the examinee that is measured via electrodes brought into contact with extremities of the body of the examinee; and the apparatus is capable of finding the lumbar circumference of the examinee, which is the circumferential size of a hip part of the examinee, by a computation based on the body data including the height and weight of the examinee and quantitative information about the body fat of the examinee measured by the body fat percent measurement means.

With this health administration apparatus according to the present invention, it is possible to automatically find the lumbar circumference of an examinee as well as to obtain information about the body fat of the examinee by the body fat percent measurement means.

A health administration apparatus according to the invention may be configured such that: the apparatus allows entry of body data of an examinee including the height and weight of the examinee;

the apparatus has body fat percent measurement means capable of finding the body fat percent of the examinee based on the impedance of the body of the examinee that is measured via electrodes brought into contact with extremities of the body of the examinee; and the apparatus is capable of finding the lumbar circumference of the examinee, which is the circumferential size of a hip part of the examinee, by a computation based on the body data including the height, weight, and body fat percent of the examinee.

With this health administration apparatus according to the invention, it is possible to automatically find the lumbar circumference of an examinee as well as to measure the body fat percent of the examinee that is usable as one of indicators of the condition of health by the body fat percent measurement means.

A health administration apparatus according to the invention may be configured such that: the apparatus allows entry of body data of an examinee including the height, weight, and age of the examinee;

the apparatus is capable of finding the lumbar circumference of the examinee which is the circumferential size of a hip part of the examinee by a computation on the body data, including the height and weight of the examinee with a predetermined computing formula;

the computing formula is created by statistical processing of correlations between the lumbar circumferences of a large number of human bodies serving as samples that are measured by a physical measurement and body data of the human bodies as the samples; and the computation with the computing formula for finding the lumbar circumference of the examinee is performed using the height, weight, and age of the examinee.

With this health administration apparatus according to the invention, it is possible to find the lumbar circumference of an examinee from the body data of the examinee including the height, weight, and age of the examinee based on the computing formula created by statistical processing of correlations between the lumbar circumferences of the large number of human bodies as the samples and the body data of the human bodies including the heights, weights, and ages of the human bodies.

Thus, it is possible to automatically find the lumbar circumference of an examinee, which is the circumferential size of a hip part of the examinee, as well as to dispense with a troublesome measuring operation such as to wrap a tape measure or the like around the hip of a human body to find the lumbar circumference in judging the degree of obesity of the human body.

A health administration apparatus according to the present invention may be configured such that: the apparatus allows entry of body data of an examinee including the height, weight, and age of the examinee;

the apparatus has body fat percent measurement means capable of finding the body fat percent of the examinee based on the impedance of the body of the examinee that is measured via electrodes brought into contact with extremities of the body of the examinee;

the apparatus is capable of finding the lumbar circumference of the examinee which is the circumferential size of a hip part of the examinee by a computation on the body data including the height, weight and body fat percent of the examinee with a predetermined computing formula;

the computing formula is created by statistical processing of correlations between the lumbar circumferences of a large number of human bodies serving as samples that are measured by a physical measurement and body data of the human bodies as the samples; and the computation with the computing formula for finding the lumbar circumference of the examinee is performed using the height, weight, age and body fat percent of the examinee.

With this health administration apparatus, it is possible to automatically find the lumbar circumference of an examinee as well as to dispense with a troublesome measuring operation using a tape measure or the like to find the lumbar circumference.

The computing formula for finding the lumbar circumference may be created on a sex basis by dividing the large number of samples into a male group and a female group. Thus, the lumbar circumference of an examinee found from the body data including the height, weight and the like of the examinee based on the computing formula can reflect differences essential to the difference in sex.

A health administration apparatus according to the invention may be configured such that: the apparatus allows entry of body data of an examinee including the height and weight of the examinee;

the apparatus is capable of finding the abdominal circumference of the examinee which is the circumferential size of a trunk part of the examinee and the lumbar circumference of the examinee which is the circumferential size of a hip part of the examinee by computations based on the body data including the height and weight; and the apparatus is capable of finding quantitative information about the visceral fat of the examinee by a computation based on the abdominal circumference and lumbar circumference found. Since the abdominal circumference and the lumbar circumference of a human body are related to the amount of visceral fat adhering to the internal organs of the human body, it is possible to obtain quantitative information about the visceral fat from the abdominal circumference and the lumbar circumference. Visceral fat strongly influences the condition of health such as adult diseases and, hence, an important indicator for the condition of health to be recognized can be obtained if such quantitative information about visceral fat is obtained.

The health administration apparatus which is capable of finding the lumbar circumference of the examinee may be configured such that: the apparatus allows entry of body data of the examinee including the height, weight and age of the examinee;

the apparatus is capable of finding the abdominal circumference of the examinee which is the circumferential size of a trunk part of the examinee by a computation on the body data based on a predetermined computing formula;

the computing formula is created by statistical processing of correlations between the abdominal circumferences of a large number of human bodies serving as samples that are measured by a physical measurement and body data of the human bodies as the samples;

the computation based on the computing formula for finding the abdominal circumference of the examinee is performed using the weight, age and BMI of the examinee;

the apparatus is capable of finding the visceral fat cross-sectional area of the examinee by a computation on the abdominal circumference and lumbar circumference found with another predetermined computing formula;

the aforesaid another computing formula is created by statistical processing of correlations between the actual visceral fat cross-sectional areas of the large number of human bodies as the samples that are measured by tomography and body data of the human bodies including WHR which is the ratio of the abdominal circumference of each of the human bodies as the samples to the lumbar circumference of that human body (abdominal circumference/lumbar circumference); and the computation with the aforesaid another computing formula for finding the visceral fat cross-sectional area is performed using the WHR of the examinee.

With this health administration apparatus, it is possible to find the visceral fat cross-sectional area of an examinee as quantitative information about the visceral fat.

The health administration apparatus which is capable of finding the lumbar circumference of the examinee may be configured such that: the apparatus allows entry of body data of the examinee including the height, weight and age of the examinee;

the apparatus is capable of finding the abdominal circumference of the examinee which is the circumferential size of a trunk part of the examinee by a computation on the body data based on a predetermined computing formula;

the computing formula is created by statistical processing of correlations between the abdominal circumferences of a large number of human bodies serving as samples that are measured by a physical measurement and body data of the human bodies as the samples;

the computation based on the computing formula for finding the abdominal circumference of the examinee is performed using the weight, age and BMI of the examinee;

the apparatus is capable of finding the visceral fat cross-sectional area of the examinee by a computation on the abdominal circumference and lumbar circumference found with another predetermined computing formula;

the apparatus has body fat percent measurement means capable of finding the body fat percent of the examinee based on the impedance of the examinee that is measured via electrodes brought into contact with extremities of the body of the examinee;

the aforesaid another computing formula is created by statistical processing of correlations between the actual visceral fat cross-sectional areas of the large number of human bodies as the samples that are measured by tomography and body data of the human bodies including WHR, which is the ratio of the abdominal circumference of each of the human bodies as the samples to the lumbar circumference of that human body (abdominal circumference/lumbar circumference), and the body fat percents of the human bodies; and the computation with the aforesaid another computing formula for finding the visceral fat cross-sectional area is performed using the WHR and body fat percent of the examinee.

With this health administration apparatus, it is possible to find the visceral fat cross-sectional area of an examinee as quantitative information about the visceral fat.

The health administration apparatus which is capable of finding the lumbar circumference of the examinee may be configured such that: the apparatus allows entry of body data of the examinee including the height, weight, and age of the examinee;

the apparatus is capable of finding the abdominal circumference of the examinee, which is the circumferential size of a trunk part of the examinee, by a computation on the body data based on a predetermined computing formula;

the computing formula is created by statistical processing of correlations between the abdominal circumferences of a large number of human bodies serving as samples that are measured by a physical measurement and body data of the human bodies as the samples;

the computation based on the computing formula for finding the abdominal circumference of the examinee is performed using the weight, age, and BMI of the examinee;

the apparatus is capable of finding the visceral fat cross-sectional area of the examinee by a computation on the abdominal circumference and lumbar circumference found with another predetermined computing formula;

the apparatus has body fat percent measurement means capable of finding the body fat percent of the examinee based on the impedance of the examinee that is measured via electrodes brought into contact with extremes of the body of the examinee;

the aforesaid another computing formula is created by statistical processing of correlations between the actual visceral fat cross-sectional areas of the large number of human bodies as the samples that are measured by tomography and body data of the human bodies including WHR, which is the ratio of the abdominal circumference of each of the human bodies as the samples to the lumbar circumference of that human body (abdominal circumference/lumbar circumference), the body fat percents of the human bodies, and the square of the ratio of the weight of each of the human bodies to the height of that human body (weight/height); and the computation with the aforesaid another computing formula for finding the visceral fat cross-sectional area is performed using the WHR and body fat percent of the examinee and the square of the ratio of the weight of the examinee to the height of the examinee (weight/height).

With this health administration apparatus, it is possible to find the visceral fat cross-sectional area of an examinee as quantitative information about the visceral fat.

The health administration apparatus, which is capable of finding the lumbar circumference of the examinee, may be configured such that: the apparatus allows entry of body data of the examinee including the height, weight, and age of the examinee;

the apparatus is capable of finding the abdominal circumference of the examinee, which is the circumferential size of a trunk part of the examinee, by a computation on the body data based on a predetermined computing formula;

the computing formula is created by statistical processing of correlations between the abdominal circumferences of a large number of human bodies serving as samples that are measured by a physical measurement and body data of the human bodies as the samples;

the computation based on the computing formula for finding the abdominal circumference of the examinee is performed using the weight, age, and BMI of the examinee;

the apparatus is capable of finding the visceral fat cross-sectional area of the examinee by a computation on the abdominal circumference and lumbar circumference found with another predetermined computing formula;

the aforesaid another computing formula is created by statistical processing of correlations between the actual visceral fat cross-sectional areas of the large number of human bodies as the samples that are measured by tomography and body data of the human bodies including WHR, which is the ratio of the abdominal circumference of each of the human bodies as the samples to the lumbar circumference of that human body (abdominal circumference/lumbar circumference), and the square of the ratio of the weight of each of the human bodies to the height of that human body (weight/height); and the computation with the aforesaid another computing formula for finding the visceral fat cross-sectional area is performed using the WHR of the examinee and the square of the ratio of the weight of the examinee to the height of the examinee (weight/height).

With this health administration apparatus, it is possible to find the visceral fat cross-sectional area of an examinee as quantitative information about the visceral fat.

The health administration apparatus which is capable of finding the lumbar circumference of the examinee may be configured such that: the apparatus allows entry of body data of the examinee including the height, weight, and age of the examinee;

the apparatus has body fat percent measurement means capable of finding the body fat percent of the examinee based on the impedance of the body of the examinee that is measured via electrodes brought into contact with extremes of the body of the examinee;

the apparatus is capable of finding the abdominal circumference of the examinee, which is the circumferential size of a trunk part of the examinee, by a computation on the body data including the height, weight, and body fat percent of the examinee based on a predetermined computing formula;

the computing formula is created by statistical processing of correlations between the abdominal circumferences of a large number of human bodies serving as samples that are measured by a physical measurement and body data of the human bodies as the samples;

the computation based on the computing formula for finding the abdominal circumference of the examinee is performed using the weight, age, body fat percent, and BMI of the examinee;

the apparatus is capable of finding the visceral fat cross-sectional area of the examinee by a computation on the abdominal circumference and lumbar circumference found with another predetermined computing formula;

the aforesaid another computing formula is created by statistical processing of correlations between the actual visceral fat cross-sectional areas of the large number of human bodies as the samples that are measured by tomography and body data of the human bodies including WHR which is the ratio of the abdominal circumference of each of the human bodies as the samples to the lumbar circumference of that human body (abdominal circumference/lumbar circumference), and the body fat percents of the human bodies; and the computation with said another computing formula for finding the visceral fat cross-sectional area is performed using the WHR and body fat percent of the examinee.

With this health administration apparatus, it is possible to find the visceral fat cross-sectional area of an examinee as quantitative information about the visceral fat.

The health administration apparatus which is capable of finding the lumbar circumference of the examinee may be configured such that: the apparatus allows entry of body data of the examinee including the height, weight, and age of the examinee;

the apparatus has body fat percent measurement means capable of finding the body fat percent of the examinee based on the impedance of the body of the examinee that is measured via electrodes brought into contact with extremes of the body of the examinee;

the apparatus is capable of finding the abdominal circumference of the examinee, which is the circumferential size of a trunk part of the examinee, by a computation on the body data including the height, weight, and body fat percent of the examinee based on a predetermined computing formula;

the computing formula is created by statistical processing of correlations between the abdominal circumferences of a large number of human bodies serving as samples that are measured by a physical measurement and body data of the human bodies as the samples;

the computation based on the computing formula for finding the abdominal circumference of the examinee is performed using the weight, age, body fat percent, and BMI of the examinee;

the apparatus is capable of finding the visceral fat cross-sectional area of the examinee by a computation on the abdominal circumference and lumbar circumference found with another predetermined computing formula;

the aforesaid another computing formula is created by statistical processing of correlations between the actual visceral fat cross-sectional areas of the large number of human bodies as the samples that are measured by tomography and body data of the human bodies including WHR, which is the ratio of the abdominal circumference of each of the human bodies as the samples to the lumbar circumference of that human body (abdominal circumference/lumbar circumference), the body fat percents of the human bodies, and the square of the ratio of the weight of each of the human bodies to the height of that human body (weight/height); and the computation with the aforesaid another computing formula for finding the visceral fat cross-sectional area is performed using the WHR and body fat percent of the examinee and the square of the ratio of the weight of the examinee to the height of the examinee (weight/height).

With this health administration apparatus, it is possible to find the visceral fat cross-sectional area of an examinee as quantitative information about the visceral fat.

The health administration apparatus which is capable of finding the lumbar circumference of the examinee may be configured such that: the apparatus allows entry of body data of the examinee including the height, weight, and age of the examinee;

the apparatus has body fat percent measurement means capable of finding the body fat percent of the examinee based on the impedance of the body of the examinee that is measured via electrodes brought into contact with extremities of the body of the examinee;

the apparatus is capable of finding the abdominal circumference of the examinee which is the circumferential size of a trunk part of the examinee by a computation on the body data including the height, weight, and body fat percent of the examinee based on a predetermined computing formula;

the computing formula is created by statistical processing of correlations between the abdominal circumferences of a large number of human bodies serving as samples that are measured by a physical measurement and body data of the human bodies as the samples;

the computation based on the computing formula for finding the abdominal circumference of the examinee is performed using the weight, age, body fat percent, and BMI of the examinee;

the apparatus is capable of finding the visceral fat cross-sectional area of the examinee by a computation on the abdominal circumference and lumbar circumference found with another predetermined computing formula;

the aforesaid another computing formula is created by statistical processing of correlations between the actual visceral fat cross-sectional areas of the large number of human bodies as the samples that are measured by tomography and body data of the human bodies including WHR, which is the ratio of the abdominal circumference of each of the human bodies as the samples to the lumbar circumference of that human body (abdominal circumference/lumbar circumference), and the square of the ratio of the weight of each of the human bodies to the height of that human body (weight/height); and the computation with the aforesaid another computing formula for finding the visceral fat cross-sectional area is performed using the WHR of the examinee and the square of the ratio of the weight of the examinee to the height of the examinee (weight/height).

With this health administration apparatus, it is possible to find the visceral fat cross-sectional area of an examinee as quantitative information about the visceral fat.

The health administration apparatus which is configured to perform the computation based on the aforesaid another computing formula using the WHR of the examinee may be arranged to form a body type judgment based on the WHR of the examinee. With this health administration apparatus, it is possible to judge the body type of an examinee based on the balance between the upper part and the lower part of the examinee's body by the WHR.

The health administration apparatus which is capable of finding the abdominal circumference of the examinee may be arranged to form an obesity judgment based on the abdominal circumference of the examinee. With this health administration apparatus, it is possible to judge whether an examinee is obese or not based on the size of the examinee's abdominal circumference found.

The health administration apparatus which is capable of finding the visceral fat cross-sectional area of the examinee may be arranged to form an obesity judgment based on the visceral fat cross-sectional area of the examinee. With this health administration apparatus, it is possible to judge whether an examinee is obese or not based on the visceral fat cross-sectional area of the examinee found.

BEST MODE FOR CARRYING OUT THE INVENTION

Figure 2:
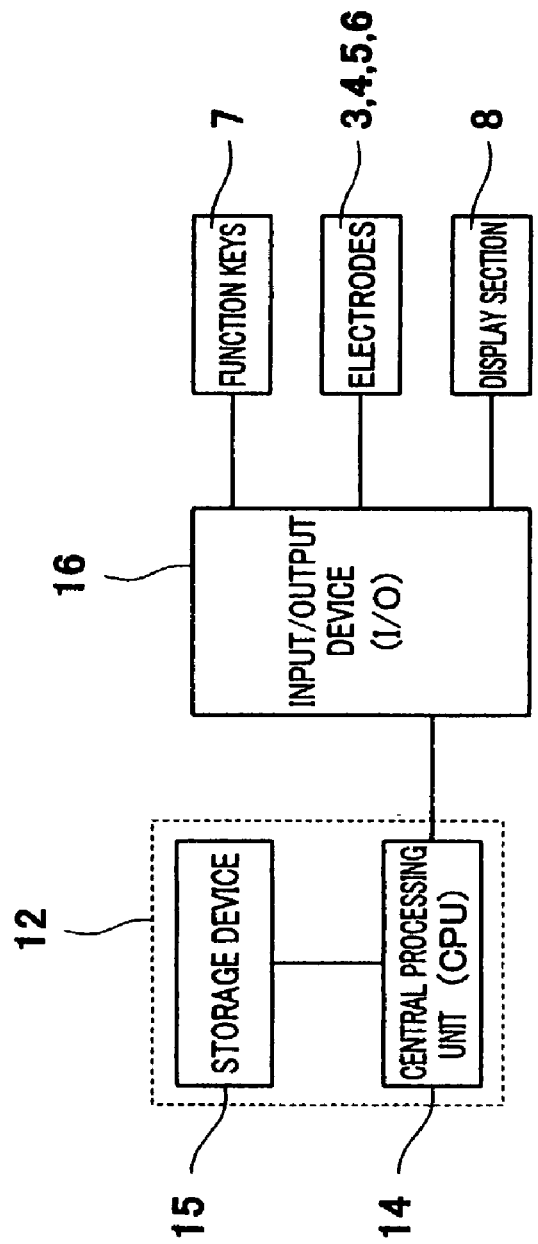
FIG. 2 is a block diagram associated with the signal processing of the health administration apparatus.
Figure 3:
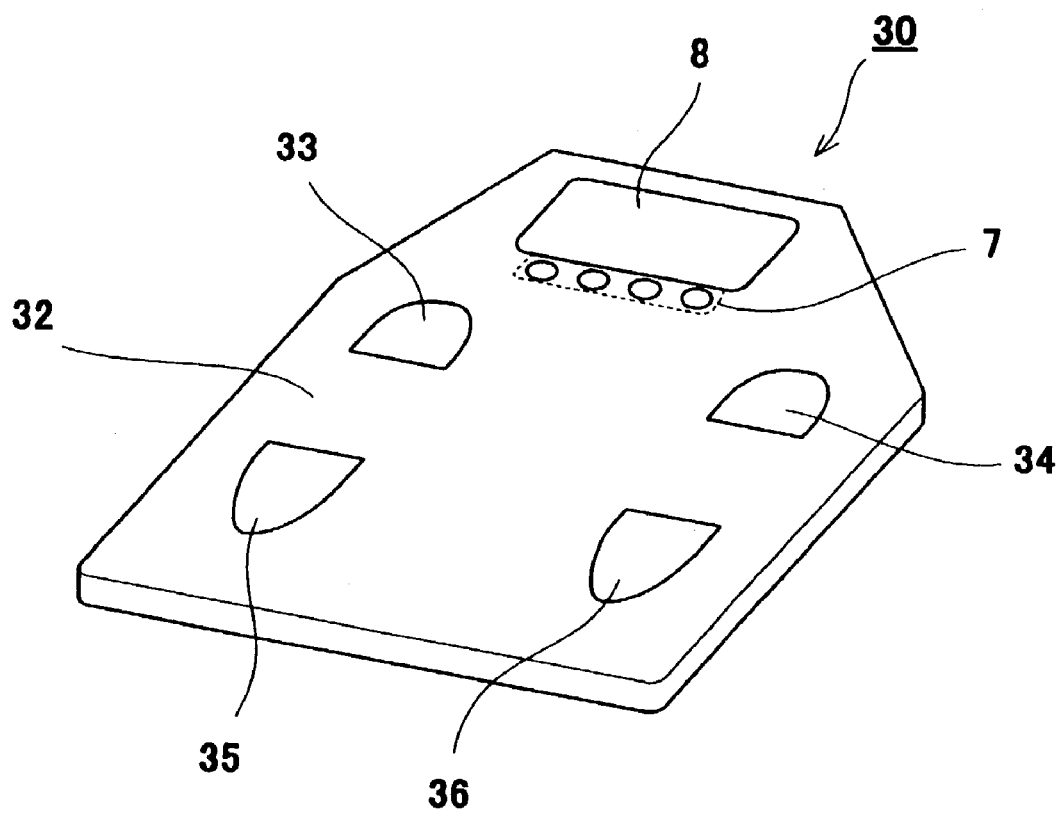
FIG. 3 is a perspective view illustrating another embodiment of the health administration apparatus.

The best mode for carrying out the present invention will be described with reference to FIGS. 1 to 3.

Figure 1:
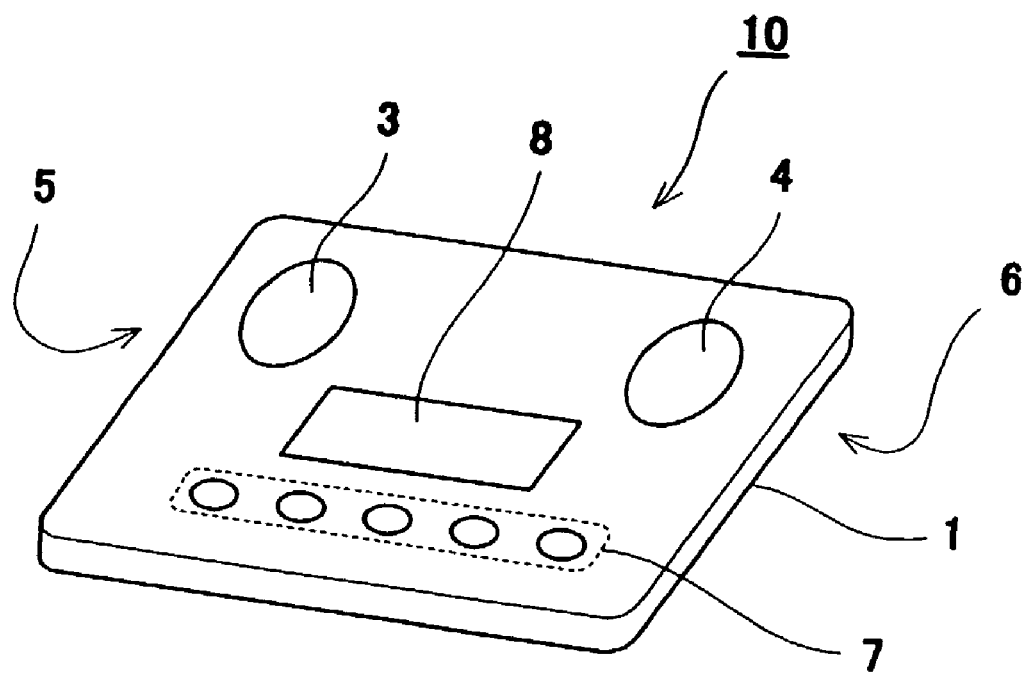
FIG. 1 is a perspective view illustrating one embodiment of a health administration apparatus.

FIG. 1 is a perspective view illustrating a health administration apparatus 10 according to one embodiment of the present invention. As will be described later, this health administration apparatus 10 is capable of finding the abdominal circumference (hereinafter referred to as "waist size" as the case may be) of an examinee, which is the circumferential size of a trunk part of the examinee and the lumbar circumference (hereinafter referred to as "hip size" as the case may be) of the examinee which is the circumferential size of a hip part of the examinee by computation.

In the health administration apparatus 10, a manipulating section 7 allows entry of body data indicative of personal body characteristics of the examinee when the examinee manipulates the manipulating section 7 and is provided with numeric keys, character keys, and the like for inputting numerals and characters. The manipulating section 7 is also provided with selection keys for selecting desired items of the body data. By manipulating the selection keys, numeric keys and the like, it is possible to input the body data.

Body data that can be inputted to the health administration apparatus 10 includes the height, weight, sex distinction data, and age of the examinee. The health administration apparatus 10 allows selective inputting of such sex distinction data according to the sex of the examinee, and the sex of the examinee is distinguished by a sex administration code corresponding to such selective inputting.

Not only the height and weight of the examinee thus inputted, but also data indicative of body characteristics, such as waist size or hip size, of the examinee found from the inputted body data by computation, is to be stored as body data in a storage device 15 to be described later.

The manipulating section 7 is further provided with an ON/OFF switch for turning the power on or off to operate the health administration apparatus 10, and an impedance measurement start switch for starting up a bioimpedance measurement to be described later.

The health administration apparatus 10 is also provided with body fat percent measurement means which is well known in the art of body fat measurement, as will be described below. The body fat percent measurement means is capable of finding quantitative information about body fat such as the percent of body fat and the weight of internal fat.

The health administration apparatus 10 has an electrode 3 disposed at a forward portion of the obverse surface of a main body 1 of the apparatus 10 on the left-hand side and an electrode 4 disposed at a forward portion of the obverse surface of the main body 1 on the right-hand side. On the reverse side of the main body 1 are disposed an electrode 5 at a location just reverse of the electrode 3 and an electrode 6 at a location just reverse of the electrode 4.

The electrode group consisting of these electrodes 3, 4, 5, and 6 is provided to measure the bioimpedance of a human body. The electrodes 5 and 6 are a pair of current path forming electrodes for forming a current path in the body of an examinee, while the electrodes 3 and 4 are a pair of voltage measuring electrodes for measuring the potential difference between two points on the current path.

The electrode group is connected to impedance measurement means (not shown) provided inside the main body 1. Specifically, the electrodes 5 and 6 are connected to a circuit part forming a constant-current source outputting a constant current, while the electrodes 3 and 4 are connected to a circuit part forming a voltmeter.

In measuring the bioimpedance of an examinee via these electrodes, it is possible that, for example, the thumb and the forefinger of the left hand of the examinee are brought into contact with the electrode 3 and the electrode 5, respectively, while the thumb and the forefinger of the right hand of the examinee are brought into contact with the electrode 4 and the electrode 6, respectively. In this way the bioimpedance of the examinee can be measured with both of the examinee's hands used as extremities of a human body.

Like the arrangement of the health administration apparatus 10, an arrangement such that the electrode 5 is disposed at a location just reverse of the electrode 3 while the electrode 6 disposed at a location just reverse of the electrode 4, has a merit that the examinee can easily hold the main body 1 while keeping two fingers of each hand in contact with the electrodes. Thus, the bioimpedance can be measured stably with the health administration apparatus 10 stably held and supported by hands. Further, it is possible that the electrodes 3 and 5 are substantially equally pressed by two fingers of one hand while the electrodes 4 and 5 substantially equally pressed by two fingers of the other hand. Thus, the bioimpedance can be measured more stably.

While quantitative information about body fat can be obtained by the body fat percent measurement means described above, the body impedance measured may be stored in the storage device 15 to be described later for use as one of personal body data items of the examinee separately from information about body fat.

A display section 8 displays body data inputted from the manipulating section 7 and a body fat percent measured by the body fat percent measurement means as well as the result of a computation such as a waist size found based on the body data inputted.

Next, a description will be made of blocks associated with the signal processing of the health administration apparatus 10 together with the operation of the health administration apparatus 10 with reference to FIG. 2. The health administration apparatus 10 has a computing section 12 comprising a central processing unit (CPU) 14 and the storage device 15 for performing various computations.

Various data and measured values stored in the storage device 15 can be displayed in the display section 8. Input/output for body data inputted, the bioimpedance and the like to be processed at the central processing unit 14 or the storage device 15 is performed through an input/output device (I/O) 16.

The storage device 15 stores body data inputted through manipulation of function keys located at the manipulating section 7 and a measured bioimpedance value obtained through the electrodes 3 to 6.

The storage device 15 previously stores a computing formula and coefficients for use in finding a body fat percent based on a measured bioimpedance by computation and, hence, the apparatus 10 is capable of finding the body fat percent of an examinee.

The storage device 15 also stores a computing formula for finding the BMI of an examinee and, hence, the apparatus 10 is capable of finding the BMI. A BMI can be found relatively easily as an indicator of obesity from the formula: (weight)/(height)$^2$.

The storage device 15 further stores a computing formula for finding a WHR, which is the ratio of the waist size to the hip size of an examinee (waist size/hip size) and, hence, the apparatus 10 is capable of finding the WHR.

Further, the storage device 15 stores the following formulae (1) to (4) as computing formulae for finding the waist size of an examinee by computation.

$$W_L = a_1 + b_1 \cdot BMI + h_1 \cdot age \quad (1)$$

$$W_L = a_2 + b_2 \cdot BMI + g_1 \cdot FAT + h_2 \cdot age \quad (2)$$

$$W_L = a_3 + b_3 \cdot BMI + c_1 \cdot W + h_3 \cdot age \quad (3)$$

$$W_L = a_4 + b_4 \cdot BMI + c_2 \cdot W + g_2 \cdot FAT + h_4 \cdot age \quad (4)$$

In the formulae (1) to (4), $W_L$ represents a waist size found from a corresponding one of the formulae. W represents the weight data of the examinee, FAT represents the body fat percent of the examinee, and age represents the age of the examinee.

The coefficients $a_n$, $b_n$, $h_n$ (n=1, ..., 4), and $c_n$ (n=1, 2) in the formulae (1) to (4) are found in the following manner separately from other data and then stored.

That is, the actual waist size of each individual of an unspecified number of human bodies serving as samples is measured by a physical measurement method. Each individual of the samples is then measured as to various items of body data to be used in the formulae (1) to (4) noted above.

Subsequently, the plurality of body data items to be used in each computing formula and the waist size are assumed to have correlations, which are then statistically processed to find the coefficients to be used in each formula.

Taking the formula (1) for example, the actual waist size measured of each individual of the samples and the BMI and age of that individual are assumed to have correlations, and the correlations are statistically processed to find $a_1$, $b_1$, and $h_1$. Here, in finding $a_1$, $b_1$, and $h_1$ the statistic processing of the correlations between two or more body data items and a waist size can be achieved by multiple linear regression analysis.

In the formula (1), the coefficient $b_1$ with respect to BMI is the first regression coefficient of BMI, the coefficient $h_1$ with respect to age is the first regression coefficient of age, and $a_1$ is the first regression coefficient of waist size.

In the same manner as with the formula (1), each of the coefficients to be used in the formulae (2) to (4) can be found by statistical processing of correlations between a waist size and body data.

In the formula (2), the coefficient $b_2$ with respect to BMI is the second regression coefficient of BMI, the coefficient $g_1$ with respect to body fat percent (FAT) is the first regression coefficient of body fat percent, the coefficient $h_2$ with respect to age is the second regression coefficient of age, and $a_2$ is the second regression coefficient of waist size.

In the formula (3), the coefficient $b_3$ with respect to BMI is the third regression coefficient of BMI, the coefficient $c_1$ with respect to weight (W) is the first regression coefficient of weight, the coefficient $h_3$ with respect to age is the third regression coefficient of age, and $a_3$ is the third regression coefficient of waist size.

In the formula (4), the coefficient $b_4$ with respect to BMI is the fourth regression coefficient of BMI, the coefficient $c_2$ with respect to weight (W) is the second regression coefficient of weight, the coefficient $g_2$ with respect to body fat percent (FAT) is the second regression coefficient of body fat percent, the coefficient $h_4$ with respect to age is the fourth regression coefficient of age, and $a_4$ is the fourth regression coefficient of waist size.

In measuring the actual waist size of an individual human body serving as a sample to create the formulae (1) to (4), it is desirable to measure the circumferential size of a trunk part at or around the fourth lumbar vertebra of the human body.

This is because the size of such a part as a waist size is considered to reflect the condition of obesity and the like of the upper part of the body of an examinee most, and because the health administration apparatus 10 can find a waist size that reflects the condition of obesity and the like of the upper part of a human body most if the size of such a part at or around the fourth lumbar vertebra of each human body of samples is collected as a waist size.

In the case of the health administration apparatus 10 there are provided two types as each of the formulae (1) to (4), one for men and the other for women. That is, the samples of human bodies are divided on a sex basis, and the statistic processing of correlations between the waist sizes and other body data of human bodies serving as samples is performed on a sex basis to create the formulae (1) to (4). Thus, the waist size of an examinee to be found from other body data of the examinee can reflect differences essential to the difference in sex more exactly. In performing computations based on the formulae (1) to (4), formulae created for men or those created for women are selected according to the sex of an examinee indicated by the sex administration code.

The number of human bodies serving as samples for collecting body data is desirably 100 or more in view of statistical processing of correlations between waist sizes and other body data. More desirably, the number of human bodies is 500 or more.

With the formula (1) it is possible to find the waist size of an examinee which reflects the BMI and the age of the examinee as body data of the examinee. With the formula (2) it is possible to find the waist size of the examinee which reflects the BMI, age, and body fat percent of the examinee. With the formula (3) it is possible to find the waist size of the examinee which reflects the BMI, weight, and age of the examinee. With the formula (4) it is possible to find the waist size of the examinee which reflects the BMI, weight, body fat percent and age of the examinee.

Of the formulae (1) to (4) noted above one for finding the waist size of an examinee from a larger number of body data items is capable of finding the waist size more accurately because it allows the body condition of the examinee to be reflected more precisely from more different angles. Specifically, the formula (4) of the formulae (1) to (4) is capable of finding the waist size of the examinee most accurately.

The storage device 15 also stores the following formulae (5) and (6) as computing formulae for finding the hip size of an examinee by computation.

$$H_L = a_{11} + c_{11} \cdot W + d_{11} \cdot T_L + h_{11} \cdot age \quad (5)$$

$$H_L = a_{12} + c_{12} \cdot W + d_{12} \cdot T_L + g_{11} \cdot FAT + h_{12} \cdot age \quad (6)$$

In the formulae (5) and (6) above, $H_L$ represents a hip size found from a corresponding one of the formulae. $T_L$ represents the height of an examinee. The coefficients an, cn, dn, hn (n=11, 12), and gn (n=11) in the formulae (5) and (6) are found in the following manner separately from other data and then stored.

That is, the actual hip size of each individual of an unspecified number of human bodies serving as samples is measured by a physical measurement method. Each individual of the samples is then measured as to various items of body data to be used in the formulae (5) and (6) noted above.

Subsequently, the plurality of body data items to be used in each computing formula and the hip size are assumed to have correlations, which are then statistically processed to find the coefficients to be used in each computing formula.

Taking the formula (5) for example, the actual hip size measured of each individual of the samples and the weight, height, and age of that individual are assumed to have correlations, and these correlations are statistically processed to find $a_{11}$, $c_{11}$, $d_{11}$, and $h_{11}$. Here, in finding $a_{11}$, $c_{11}$, $d_{11}$, and $h_{11}$ the statistical processing of correlations between two or more body data items and a hip size can be achieved by multiple linear regression analysis.

In the formula (5), the coefficient $c_{11}$ with respect to weight (W) is the eleventh regression coefficient of weight, the coefficient $d_{11}$ with respect to height ($T_L$) is the eleventh regression coefficient of height, the coefficient $h_{11}$ with respect to age is the eleventh regression coefficient of age, and $a_{11}$ is the eleventh regression coefficient of hip size.

In the same manner as with the formula (5), the coefficients to be used in the formula (6) can be found by statistical processing of correlations between a waist size and body data.

In the formula (6), the coefficient $c_{12}$ with respect to weight (W) is the twelfth regression coefficient of weight, the coefficient $d_{12}$ with respect to height ($T_L$) is the twelfth regression coefficient of height, the coefficient $g_{11}$ with respect to body fat percent (FAT) is the eleventh regression coefficient of body fat percent, the coefficient $h_{12}$ with respect to age is the twelfth regression coefficient of age, and $a_{12}$ is the twelfth regression coefficient of hip size.

In measuring the actual waist size of each individual of human bodies serving as samples to create the formulae (5) and (6), it is desirable to measure the circumferential size of near the thickest part of the hip of the examinee.

This is because the size of such a part as a hip size is considered to reflect the condition of obesity and the like of the lower part of the body of an examinee most, and because the health administration apparatus 10 can find a waist size that reflects the condition of obesity and the like of the lower part of a human body most if the sizes of such thickest parts of the hips of human bodies serving as the samples are collected as hip sizes.

In the case of the health administration apparatus 10, there are provided two types as each of the formulae (5) and (6), one for men and the other for women. That is, the samples of human bodies are divided on a sex basis, and statistical processing of correlations between the hip sizes and other body data of the human bodies serving as samples is performed on a sex basis to create the formulae (5) and (6). Thus, the hip size of an examinee to be found from other body data of the examinee can reflect differences essential to the difference in sex more exactly. In performing computations based on the formulae (5) and (6), the formulae of the type created for men or those of the type created for women are selected according to the sex of the examinee indicated by the sex administration code.

The number of human bodies as samples for collecting body data is desirably 100 or more in view of statistical processing of correlations between the hip sizes and other body data of the human bodies. More desirably, the number of human bodies is 500 or more.

The physical measurement method for measuring the waist sizes and hip sizes of human bodies serving as the samples in creating the formulae (1) to (6) described above may be any method by which the length (size) of the waist or hip part of concern can be measured. Specifically, it is possible to employ any method which is capable of measuring the length of a body part of concern as a physical quantity such as a method of directly measuring such a part by wrapping a tape measure around a human body as a sample or an automatic measurement method using light.

The storage device 15 also stores a computing formula for finding a WHR (waist size/hip size) based on waist size and hip size found with the formulae (1) to (6), the WHR being the ratio of the waist size to the hip size and, hence, the apparatus 10 is capable of finding the WHR.

Further, the storage device 15 stores the following formulae (7) to (11) as computing formulae for finding a visceral fat cross-sectional area as quantitative information about the visceral fat of an examinee by computation.

$$VA = i_1 \cdot W_L + j_1 \quad (7)$$

$$VA = k_1 \cdot WHR + j_2 \quad (8)$$

$$VA = k_2 \cdot WHR + g_{21} \cdot FAT + j_3 \quad (9)$$

$$VA = k_3 \cdot WHR + f_{21} \cdot (W/T_L)^2 + j_4 \quad (10)$$

$$VA = k_4 \cdot WHR + f_{22} \cdot (W/T_L)^2 + g_{22} \cdot FAT + j_5 \quad (11)$$

In the formulae (1) to (4), VA represents a visceral fat cross-sectional area found from a corresponding one of the formulae. The coefficients in (n=1), jn (n=1, . . . , 5), kn (n=1, . . . , 4), fn, and gn (n=21, 22) in the formulae (7) to (11) are found in the following manner separately from other data and then stored.

That is, the actual visceral fat cross-sectional area of each individual of an unspecified number of human bodies serving as samples is measured. Each individual of the samples is then measured as to various items of body data to be used in the formulae (7) to (11) noted above.

Subsequently, the plurality of body data items to be used in each of the computing formulae and the visceral fat cross-sectional area are assumed to have correlations, which are then statistically processed to find the coefficients to be used in each of the computing formulae.

Taking the formula (11) for example, the actual cross-sectional area measured of the visceral fat of each individual of the samples and the WHR, (weight/height)$^2$ and body fat percent of that individual is assumed to have correlations, and these correlations are statistically processed to find $k_4$, $f_{22}$, $g_{22}$, and $j_5$. In finding $k_4$, $f_{22}$, $g_{22}$, and $j_5$ the statistic processing of correlations between two or more body data items and a visceral fat cross-sectional area can be achieved by multiple linear regression analysis.

In the formula (11), the coefficient $k_4$ with respect to WHR is the fourth regression coefficient of WHR, the coefficient $f_{22}$ with respect to $(W/T_L)^2$ is the 22nd regression coefficient of $(W/T_L)^2$, the coefficient $g_{22}$ with respect to body fat percent (FAT) is the 22nd regression coefficient of body fat percent, and $j_5$ is the fifth regression coefficient of the visceral fat cross-sectional area.

In the same manner as with the formula (11), the coefficients to be used in the formulae (7) to (10) can be found by statistical processing of correlations between the visceral fat cross-sectional area and body data.

In the formula (7), the coefficient $i_1$ with respect to waist size ($W_L$) is the first regression coefficient of waist size, and $j_1$ is the first regression coefficient of visceral fat cross-sectional area.

In the formula (8), the coefficient $k_1$ with respect to WHR is the first regression coefficient of WHR, and $j_2$ is the second regression coefficient of visceral fat cross-sectional area.

In the formula (9), the coefficient $k_2$ with respect to WHR is the second regression coefficient of WHR, the coefficient $g_{21}$ with respect to body fat percent (FAT) is the 21st regression coefficient of body fat percent, and $j_3$ is the third regression coefficient of visceral fat cross-sectional area.

In the formula (10), the coefficient $k_3$ with respect to WHR is the third regression coefficient of WHR, the coefficient $f_{21}$ with respect to $(W/T_L)^2$ is the 21st regression coefficient of $(W/T_L)^2$, and $j_4$ is the fourth regression coefficient of visceral fat cross-sectional area.

Here, the measurement of the actual visceral fat cross-sectional area of a human body serving as a sample can be achieved by tomography. It is possible to use various tomographic methods that are capable of accurately measuring a cross-section of an abdominal part of a human body such as CT-scan, MRI, and ultrasonic diagnostics.

In the case of the health administration apparatus 10, there are provided two types as each of the formulae (7) to and (11), one for men and the other for women. That is, the samples of human bodies are divided on a sex basis, and statistical processing of correlations between the visceral fat cross-sectional areas and other body data of the human bodies serving as samples is performed on a sex basis to create the formulae (7) to (11). Thus, the visceral fat cross-sectional area of an examinee to be found from other body data of the examinee can reflect differences essential to the difference in sex more exactly. In performing computations with the formulae (7) to (11), the formulae of the type created for men or those of the type created for women are selected according to the sex of the examinee indicated by the sex administration code.

The number of human bodies as the samples for collecting body data is desirably 100 or more in view of statistical processing of correlations between the visceral fat cross-sectional areas and other body data of the human bodies. More desirably, the number of human bodies is 500 or more.

Still further, the storage device 15 is configured to pre-store criterial values of waist size, WHR, and visceral fat cross-sectional area for judging the body type of an examinee. The criterial value of waist size established for judging the body type of a man is 85 cm, while that established for judging the body type of a woman is 90 cm. The criterial value of WHR established for men is 1.0, while that established for women is 0.8. For men and women both, the criterial value of visceral fat cross-sectional area established is 100 cm$^2$.

The waist size, WHR, and visceral fat cross-sectional area found on an examinee are compared with respective criterial values established to judge the obesity and body type of the examinee in the following manner.

That is, a man having a waist size of 85 cm or more and a woman having a waist size of 90 cm or more are judged to be of a body type that is obese at the upper part of the body. A man having a WHR of less than 1.0 and a woman having a WHR of less than 0.8 are judged to be of a body type that is obese at the lower part of the body. A man and a woman are both judged to be of the visceral fat type obesity if their respective visceral fat cross-sectional areas are 100 cm$^2$ or more.

The health administration apparatus 10 having been described above is an example that is configured to allow the user to hold it by his or her hands for manipulation. A health administration apparatus according to the present invention may comprise a single apparatus capable of functioning not only as a health administration apparatus but also as a weighing machine. Health administration apparatus 30 shown in FIG. 3 is incorporated with weight measurement means so that the apparatus 30 functions also as a weighing machine.

The health administration apparatus 30 has a main body formed with a weight measurement surface 32 on the obverse side thereof, and a load cell not shown that is disposed inside the main body to detect a weight on the weight measurement surface 32. Thus, when an examinee steps onto the weight measurement surface 32, the weight of the examinee can be measured.

The weight measurement surface 32 is provided with electrodes 33, 34, 35, and 36 for measuring the bioimpedance of an examinee. The electrodes 33 and 34 are a pair of current path forming electrodes for forming a current path by passing current through the body of the examinee, while the electrodes 35 and 36 are a pair of voltage measuring electrodes for measuring the voltage between two points on the current path.

As with the health administration apparatus 30, the electrodes 33, 34, 35, and 36 are connected to impedance measurement means provided inside the main body, the impedance measurement means being well known in the art of impedance measurement; thus, the impedance of a human body can be measured via the electrodes 33, 34, 35, and 36.

When an examinee steps onto the measurement surface 32 with his or her left sole brought into contact with the electrodes 33 and 35 and his or her right sole brought into contact with the electrodes 34 and 36, the apparatus 30 can measure the weight of the examinee as well as the bioimpedance of the examinee with his or her both feet serving as extremes of the human body.

The health administration apparatus 30 is provided with manipulating section 7 and display section 8 which are configured similarly to those of the health administration apparatus 10 described earlier. Further, the health administration apparatus 30 is provided therein with a computing section 12 comprising central processing unit 14 and storage device 15 not particularly shown in FIG. 3.

The storage device 15, which is configured similarly to that of the health administration apparatus 10 described earlier, is adapted to store inputted data, results of measurements and results of computations. Computations for finding BMI and WHR and computations with the foregoing formulae (1) to (11) are performed by the computing section 12.

The weight of an examinee detected by the load cell disposed inside the health administration apparatus 30 is processed as weight data by the computing section 12. Thus, with the health administration apparatus 30 there is no need to manipulate the manipulating section 7 in inputting the weight of the examinee and, hence, it is possible to reduce the number of body data items to be inputted through the manipulating section 7 and to lighten the burden of such manipulation.

INDUSTRIAL APPLICABILITY

As has been described above, the health administration apparatus of the present invention provides the effect that an abdominal circumference or a lumbar circumference can be found automatically. With the health administration apparatus it is possible to dispense with a troublesome operation such as to wrap a tape measure or the like around a part of concern of a human body to measure an abdominal circumference or a lumbar circumference in judging the condition of health based on a degree of obesity.

The invention claimed is:

1. A health administration apparatus comprising:
an input device configured to receive input of body data of an examinee including the height and weight of the examinee;
impedance measurement device for measuring the impedance of the body of the examinee;
a computing section including a storage device configured to store a formula for computing the abdominal circumference of an examinee based on body data of the examinee including the height and weight of the examinee, and based on the measured impedance of the body of the examinee, and a processing unit configured to apply the formula to compute the abdominal circumference of the examinee based on the inputted body data including the height and weight of the examinee, the computed abdominal circumference being an estimated circumferential size of a trunk part of the examinee; and
a display section configured to display the computed abdominal circumference.

2. The health administration apparatus according to claim 1, wherein the computing section is further configured to find a visceral fat cross-sectional area by a computation based on the abdominal circumference found.

3. The health administration apparatus according to claim 2, wherein the computing section is further configured to form an obesity judgment based on the visceral fat cross-sectional area found.

4. The health administration apparatus according to claim 1, wherein the computing section is further configured to form an obesity judgment based on the abdominal circumference of the examinee.

5. The health administration apparatus according to claim 1, wherein the computing section is further configured to find the visceral fat cross-sectional area of the examinee by a computation on the abdominal circumference found with a predetermined computing formula;
wherein said predetermined computing formula is created by statistical processing of correlations between the actual visceral fat cross-sectional areas, as measured by tomography, of a statistical sample of human bodies, and the abdominal circumferences of the human bodies in the sample.

6. A health administration apparatus comprising:
an input device configured to receive entry of body data of an examinee including the height and weight of the examinee;
impedance measurement means for measuring the impedance of the body of the examinee via electrodes brought into contact with extremities of the body of the examinee;
a storage device configured to store a formula for computing the abdominal circumference of an examinee based on body data of the examinee including the height, weight, and impedance of the body of the examinee;
a processing unit configured to apply this formula to compute the abdominal circumference of the examinee based on entered body data including the height and weight, and measured impedance of the body of the examinee, the computed abdominal circumference being an estimated circumferential size of a trunk part of the examinee; and a display section configured to display the computed abdominal circumference.

7. A health administration apparatus comprising:

an input device configured to receive entry of body data of an examinee including the height and weight of the examinee;

body fat percent measurement means for finding the body fat percent of the examinee based on the impedance of the body of the examinee that is measured via electrodes brought into contact with extremities of the body of the examinee;

a storage device configured to store a formula for computing the abdominal circumference of an examinee based on body data of the examinee including the height and weight of the examinee and information about the body fat of the examinee measured by the body fat percent measurement means;

a processing unit configured to apply this formula to compute the abdominal circumference of the examinee based on entered body data including the height and weight of the examinee and information about the body fat of the examinee measured by the body fat percent measurement means, the computed abdominal circumference being an estimated circumferential size of a trunk part of the examinee; and a display section configured to display the computed abdominal circumference.

8. The health administration apparatus according to claim 7, wherein the processing unit is configured to compute a visceral fat cross-sectional area by a computation based on the computed abdominal circumferences, according to a predetermined computing formula.

9. The health administration apparatus according to claim 7, wherein said predetermined computing formula is created by statistical processing of correlations between the actual visceral fat cross-sectional areas, as measured by tomography, of a statistical sample of human bodies, and the abdominal circumferences of the human bodies in the sample.

10. The health administration apparatus according to claim 7, wherein the processing unit is configured to form an obesity judgment based on the abdominal circumference of the examinee.

11. The health administration apparatus according to claim 8, wherein the processing unit is configured to form an obesity judgment based on the visceral fat cross-sectional area found.

12. A health administration apparatus comprising:

an input device configured to receive entry of body data of an examinee including the height and weight of the examinee;

body fat percent measurement means for finding the body fat percent of the examinee based on the impedance of the body of the examinee that is measured via electrodes brought into contact with extremes of the body of the examinee;

a storage section configured to store a formula for computing the abdominal circumference of an examinee based on body data of the examinee including the height and weight of the examinee and the measured body fat percent; and a processing unit configured to apply this formula to compute the abdominal circumference of the examinee based on entered body data including the height and weight of the examinee and measured body fat percent, the computed abdominal circumference being an estimated circumferential size of a trunk part of the examinee; and a display section configured to display the computed abdominal circumference.

13. A health administration apparatus comprising:

an input device configured to receive entry of body data of an examinee including the height, weight, and age of the examinee;

a computing section configured to compute the abdominal circumference of the examinee, which is the circumferential size of a trunk part of the examinee, by a computation of a first predetermined computing formula, wherein the first predetermined computing formula calculates abdominal circumference based on weight, age, and BMI of the examinee; and a display section configured to display the computed abdominal circumference;

wherein the first computing formula is created by statistical processing of correlations between the abdominal circumferences of a large number of human bodies serving as samples that are measured by a physical measurement and body data of the human bodies as the samples.

14. The health administration apparatus according to claim 13, wherein the computing section is configured to compute a visceral fat cross-sectional area by a computation based on the computed abdominal circumference.

15. The health administration apparatus according to claim 14, wherein the computing section is further configured to compute the visceral fat cross-sectional area of the examinee by a computation of a second predetermined computing formula based on the computed abdominal circumference;

wherein said second predetermined computing formula is created by statistical processing of correlations between the actual visceral fat cross-sectional areas of the large number of human bodies as the samples that are measured by tomography and the abdominal circumferences of the human bodies as the samples.

16. The health administration apparatus according to claim 13, wherein the computing section is further configured to form an obesity judgment based on the abdominal circumference of the examinee.

17. The health administration apparatus according to claim 14, wherein the computing section is further configured to form an obesity judgment based on the computed visceral fat cross-sectional area.

18. The health administration apparatus according to claim 13, wherein the computing formula for finding the abdominal circumference is created on a sex basis by dividing the large number of samples to be used in creating the computing formula into a male group and a female group.

19. A health administration apparatus comprising:

an input device configured to receive entry of body data of an examinee including the height, weight, and age of the examinee;

body fat percent measurement means for finding the body fat percent of the examinee based on the impedance of the body of the examinee that is measured via electrodes brought into contact with extremities of the body of the examinee; and a computing section configured to compute the abdominal circumference of the examinee, which is the circumferential size of a trunk part of the examinee, by a computation of a predetermined formula, wherein the predetermined formula calculates abdominal circumference of the examinee based on height, weight, age, body fat percent, and BMI; and
a display section configured to display the computed abdominal circumference;
wherein the computing formula is created by statistical processing of correlations between the abdominal circumferences of a large number of human bodies serving as samples that are measured by a physical measurement and body data of the human bodies as the samples.

20. The health administration apparatus according to claim 19, wherein the computing formula for finding the abdominal circumference is created on a sex basis by dividing the large number of samples to be used in creating the computing formula into a male group and a female group.

21. A health administration apparatus comprising:
an input device configured to receive entry of body data of an examinee including the height and weight of the examinee;
a computing section configured to compute the lumbar circumference of the examinee, which is the circumferential size of a hip part of the examinee, by a computation of a first predetermined computing formula that calculates the lumbar circumference based on the height and weight of the examinee; and
a display section configured to display the computed lumbar circumference.

22. The health administration apparatus according to claim 21,
wherein the input device is further configured to receive entry of an age of the examinee;
wherein the computing section is further configured to compute the abdominal circumference of the examinee, which is the circumferential size of a trunk part of the examinee, by a computation of a second predetermined computing formula that calculates the abdominal circumference based on weight, age, and BMI of the examinee;
wherein the computing formula is created by statistical processing of correlations between the abdominal circumferences of a large number of human bodies serving as samples that are measured by a physical measurement and body data of the human bodies as the samples;
wherein the computing section is further configured to compute the visceral fat cross-sectional area of the examinee by a computation of a third predetermined computing formula, based on the computed abdominal circumference and lumbar circumference;
wherein said third predetermined computing formula is created by statistical processing of correlations between the actual visceral fat cross-sectional areas of the large number of human bodies as the samples that are measured by tomography and body data of the human bodies including WHR, which is the ratio of the abdominal circumference of each of the human bodies as the samples to the lumbar circumference of that human body (abdominal circumference/lumbar circumference);
wherein the computation of said third predetermined computing formula for finding the visceral fat cross-sectional area is performed using the WHR of the examinee; and
wherein the display section is further configured to display the computed abdominal circumference.

23. The health administration apparatus according to claim 22, wherein the computing section is further configured to form a body type judgment based on the WHR of the examinee.

24. The health administration apparatus according to claim 21,
wherein the input device is further configured to receive an age of the examinee;
wherein the computing section is further configured to compute the abdominal circumference of the examinee, which is the circumferential size of a trunk part of the examinee, by a computation of a second predetermined computing formula that calculates the abdominal circumference based on the entered weight and age, and a calculated BMI of the examinee;
wherein the second predetermined computing formula is created by statistical processing of correlations between the abdominal circumferences of a large number of human bodies serving as samples that are measured by a physical measurement and body data of the human bodies as the samples;
wherein the computing section is further configured to compute the visceral fat cross-sectional area of the examinee by a computation of a third predetermined computing formula based on the computed abdominal circumference and lumbar circumference;
wherein the apparatus has body fat percent measurement means for finding the body fat percent of the examinee based on the impedance of the examinee that is measured via electrodes brought into contact with extremities of the body of the examinee;
wherein said third predetermined computing formula is created by statistical processing of correlations between the actual visceral fat cross-sectional areas of the large number of human bodies as the samples that are measured by tomography and body data of the human bodies, including WHR which is the ratio of the abdominal circumference of each of the human bodies as the samples to the lumbar circumference of that human body (abdominal circumference/lumbar circumference), and the body fat percents of the human bodies;
wherein the computation of said third predetermined computing formula for finding the visceral fat cross-sectional area is performed using the WHR and body fat percent of the examinee; and
wherein the display section is further configured to display the computed abdominal circumference.

25. The health administration apparatus according to claim 21,
wherein the input device is further configured to receive entry of an age of the examinee;
wherein the computing section is further configured to compute the abdominal circumference of the examinee, which is the circumferential size of a trunk part of the examinee, by a computation of a second predetermined computing formula that calculates the abdominal circumference based on the entered weight and age, and a calculated BMI of the examinee;
wherein the computing formula is created by statistical processing of correlations between the abdominal circumferences of a large number of human bodies serving as samples that are measured by a physical measurement and body data of the human bodies as the samples;
wherein the computing section is configured to compute the visceral fat cross-sectional area of the examinee by a computation of a third predetermined computing formula based on the computed abdominal circumference and lumbar circumference;

wherein the apparatus further comprises body fat percent measurement means for finding the body fat percent of the examinee based on the impedance of the examinee that is measured via electrodes brought into contact with extremities of the body of the examinee;

wherein said third predetermined computing formula is created by statistical processing of correlations between the actual visceral fat cross-sectional areas of the large number of human bodies as the samples that are measured by tomography and body data of the human bodies including WHR, which is the ratio of the abdominal circumference of each of the human bodies as the samples to the lumbar circumference of that human body (abdominal circumference/lumbar circumference), the body fat percents of the human bodies, and the square of the ratio of the weight of each of the human bodies to the height of that human body (weight/height);

wherein the computation of said third computing formula for finding the visceral fat cross-sectional area is performed using the WHR and body fat percent of the examinee and the square of the ratio of the weight of the examinee to the height of the examinee (weight/height); and wherein the display section is further configured to display the computed abdominal circumference.

26. The health administration apparatus according to claim 21, wherein the input device is further configured to receive entry of an age of the examinee;

wherein the computing section is further configured to compute the abdominal circumference of the examinee, which is the circumferential size of a trunk part of the examinee, by a computation of a second predetermined computing formula that calculates the abdominal circumference based on the entered weight and age, and a calculated BMI of the examinee;

wherein the computing formula is created by statistical processing of correlations between the abdominal circumferences of a large number of human bodies serving as samples that are measured by a physical measurement and body data of the human bodies as the samples;

wherein the computing section is configured to compute the visceral fat cross-sectional area of the examinee by a computation of a third predetermined computing formula based on the computed abdominal circumference and lumbar circumference;

wherein said third computing formula is created by statistical processing of correlations between the actual visceral fat cross-sectional areas of the large number of human bodies as the samples that are measured by tomography and body data of the human bodies including WHR, which is the ratio of the abdominal circumference of each of the human bodies as the samples to the lumbar circumference of that human body (abdominal circumference/lumbar circumference), and the square of the ratio of the weight of each of the human bodies to the height of that human body (weight/height);

wherein the computation of said third computing formula for finding the visceral fat cross-sectional area is performed using the WHR of the examinee and the square of the ratio of the weight of the examinee to the height of the examinee (weight/height); and wherein the display section is further configured to display the computed abdominal circumference.

27. The health administration apparatus according to claim 21, wherein the input device is further configured to receive entry of an age of the examinee;

wherein the apparatus further comprises body fat percent measurement means for finding the body fat percent of the examinee based on the impedance of the body of the examinee that is measured via electrodes brought into contact with extremities of the body of the examinee;

wherein the computing section is further configured to compute the abdominal circumference of the examinee, which is the circumferential size of a trunk part of the examinee, by a computation of a second predetermined computing formula that calculates the abdominal circumference based on the entered weight and age, the body fat percent and a calculated BMI of the examinee;

wherein the computing formula is created by statistical processing of correlations between the abdominal circumferences of a large number of human bodies serving as samples that are measured by a physical measurement and body data of the human bodies as the samples;

wherein the computing section is further configured to compute the visceral fat cross-sectional area of the examinee by a computation of a third predetermined computing formula based on the computed abdominal circumference and lumbar circumference;

wherein said third predetermined computing formula is created by statistical processing of correlations between the actual visceral fat cross-sectional areas of the large number of human bodies as the samples that are measured by tomography and body data of the human bodies including WHR, which is the ratio of the abdominal circumference of each of the human bodies as the samples to the lumbar circumference of that human body (abdominal circumference/lumbar circumference), and the body fat percents of the human bodies;

wherein the computation of said third predetermined computing formula for finding the visceral fat cross-sectional area is performed using the WHR and body fat percent of the examinee; and wherein the display section is further configured to display the computed abdominal circumference.

28. The health administration apparatus according to claim 21, wherein the input device is further configured to receive entry of age of the examinee;

wherein the apparatus further comprises body fat percent measurement means for finding the body fat percent of the examinee based on the impedance of the body of the examinee that is measured via electrodes brought into contact with extremities of the body of the examinee;

wherein the computing section is further configured to compute the abdominal circumference of the examinee, which is the circumferential size of a trunk part of the examinee, by a computation of a second predetermined computing formula that calculates the abdominal circumference based on the entered weight and age, the body fat percent, and a calculated BMI of the examinee;

wherein the computing formula is created by statistical processing of correlations between the abdominal circumferences of a large number of human bodies serving as samples that are measured by a physical measurement and body data of the human bodies as the samples;

wherein the computing section is configured to compute the visceral fat cross-sectional area of the examinee by a computation of a third predetermined computing formula based on the abdominal circumference and lumbar circumference;

wherein said third predetermined computing formula is created by statistical processing of correlations between the actual visceral fat cross-sectional areas of the large number of human bodies as the samples that are measured by tomography and body data of the human bodies including WHR, which is the ratio of the abdominal circumference of each of the human bodies as the samples to the lumbar circumference of that human body (abdominal circumference/lumbar circumference), the body fat percents of the human bodies, and the square of the ratio of the weight of each of the human bodies to the height of that human body (weight/height);

wherein the computation of said third predetermined computing formula for finding the visceral fat cross-sectional area is performed using the WHR and body fat percent of the examinee and the square of the ratio of the weight of the examinee to the height of the examinee (weight/height); and wherein the display section is further configured to display the computed abdominal circumference.

29. The health administration apparatus according to claim 21, wherein the input device is further configured to receive entry of age of the examinee;

wherein the apparatus further comprises body fat percent measurement means for finding the body fat percent of the examinee based on the impedance of the body of the examinee that is measured via electrodes brought into contact with extremities of the body of the examinee;

wherein the computing section is further configured to compute the abdominal circumference of the examinee, which is the circumferential size of a trunk part of the examinee, by a computation of a second predetermined computing formula that calculates the abdominal circumference based on the entered weight and age, the body fat percent, and a calculated BMI of the examinee;

wherein the computing formula is created by statistical processing of correlations between the abdominal circumferences of a large number of human bodies serving as samples that are measured by a physical measurement and body data of the human bodies as the samples;

wherein the computing section is further configured to compute the visceral fat cross-sectional area of the examinee by a computation of a third predetermined computing formula based on the abdominal circumference and lumbar circumference;

said third predetermined computing formula is created by statistical processing of correlations between the actual visceral fat cross-sectional areas of the large number of human bodies as the samples that are measured by tomography and body data of the human bodies including WHR, which is the ratio of the abdominal circumference of each of the human bodies as the samples to the lumbar circumference of that human body (abdominal circumference/lumbar circumference), and the square of the ratio of the weight of each of the human bodies to the height of that human body (weight/height);

the computation of said third predetermined computing formula for finding the visceral fat cross-sectional area is performed using the WHR of the examinee and the square of the ratio of the weight of the examinee to the height of the examinee (weight/height); and wherein the display section is further configured to display the computed abdominal circumference.

30. A health administration apparatus comprising:

an input device configured to receive entry of body data of an examinee, including the height and weight of the examinee;

impedance measurement means for measuring the impedance of the body of the examinee via electrodes brought into contact with extremes of the body of the examinee;

a computing section configured to compute the lumbar circumference of the examinee, which is the circumferential size of a hip part of the examinee, by a computation of a predetermined computing formula that calculates the lumbar circumference based on the height, weight, and impedance of the examinee; and a display section configured to display the computed lumbar circumference.

31. A health administration apparatus comprising:

an input device configured to receive entry of body data of an examinee including the height and weight of the examinee;

body fat percent measurement means for finding the body fat percent of the examinee based on the impedance of the body of the examinee that is measured via electrodes brought into contact with extremities of the body of the examinee;

a computing section configured to compute the lumbar circumference of the examinee, which is the circumferential size of a hip part of the examinee, by a computation of a predetermined computing formula that calculates the lumbar circumference based on the body data including the height and weight of the examinee and quantitative information about the body fat of the examinee measured by the body fat percent measurement means; and a display section configured to display the computed lumbar circumference.

32. A health administration apparatus comprising:

an input device configured to receive entry of body data of an examinee including the height and weight of the examinee;

body fat percent measurement means for finding the body fat percent of the examinee based on the impedance of the body of the examinee that is measured via electrodes brought into contact with extremities of the body of the examinee;

a computing section configured to compute the lumbar circumference of the examinee, which is the circumferential size of a hip part of the examinee, by a computation of a predetermined computing formula that calculates the lumbar circumference based on the body data including the height, weight, and body fat percent of the examinee; and a display section configured to display the computed lumbar circumference.

33. A health administration apparatus comprising:

an input device configured to receive entry of body data of an examinee including the height, weight, and age of the examinee;

a computing section configured to compute the lumbar circumference of the examinee, which is the circumferential size of a hip part of the examinee, by a computation of a predetermined computing formula that calculates the lumbar circumference based on the height, weight and age of the examinee; and a display section configured to display the computed lumbar circumference;

wherein the computing formula is created by statistical processing of correlations between the lumbar circumferences of a large number of human bodies serving as samples that are measured by a physical measurement and body data of the human bodies as the samples.

34. The health administration apparatus according to claim 33, wherein the computing formula for finding the lumbar circumference is created on a sex basis by dividing the large number of samples to be used in creating the computing formula into a male group and a female group.

35. A health administration apparatus comprising:

an input device configured to receive entry of body data of an examinee including the height, weight, and age of the examinee;

body fat percent measurement means for finding the body fat percent of the examinee based on the impedance of the body of the examinee that is measured via electrodes brought into contact with extremities of the body of the examinee;

a computing section configured to compute a lumbar circumference of the examinee, which is the circumferential size of a hip part of the examinee, by a computation of a predetermined computing formula that calculates the lumbar circumference based on height, weight, age, and body fat percent of the examinee; and a display section configured to display the computed lumbar circumference;

wherein the computing formula is created by statistical processing of correlations between the lumbar circumferences of a large number of human bodies serving as samples that are measured by a physical measurement and body data of the human bodies as the samples.

36. The health administration apparatus according to claim 35, wherein the computing formula for finding the lumbar circumference is created on a sex basis by dividing the large number of samples to be used in creating the computing formula into a male group and a female group.

37. A health administration apparatus comprising:

an input device configured to receive entry of body data of an examinee including the height and weight of the examinee;

a computing section configured to compute the abdominal circumference of the examinee, which is the circumferential size of a trunk part of the examinee, and the lumbar circumference of the examinee, which is the circumferential size of a hip part of the examinee, by computations of respective predetermined computing formulas based on the height and weight of the examinee; and a display section configured to display the computed abdominal circumference and lumbar circumference;

wherein the computing section is configured to compute quantitative information about the visceral fat of the examinee by a computation based on the computed abdominal circumference and lumbar circumference.

* * * * *